United States Patent [19]

Chan

[11] 4,310,463

[45] Jan. 12, 1982

[54] 3-(N-ARYLAMINO)-GAMMA-BUTYROLACTONES, BUTYROLACTAMS AND THIOBUTYROLACTONES ARE INTERMEDIATES FOR COMPOUNDS HAVING FUNGICIDAL ACTIVITY

[75] Inventor: David C. K. Chan, Petaluma, Calif.

[73] Assignee: Chevron Research, San Francisco, Calif.

[21] Appl. No.: 68,243

[22] Filed: Aug. 17, 1979

Related U.S. Application Data

[63] Continuation-in-part of Ser. No. 13,856, Feb. 2, 1979, which is a continuation-in-part of Ser. No. 847,502, Nov. 1, 1977, abandoned, which is a continuation-in-part of Ser. No. 837,121, Sep. 29, 1977, Pat. No. 4,141,989, which is a continuation-in-part of Ser. No. 731,491, Oct. 12, 1976, Pat. No. 4,107,323, which is a continuation-in-part of Ser. No. 631,351, Nov. 12, 1975, Pat. No. 4,012,519, which is a continuation-in-part of Ser. No. 548,660, Feb. 10, 1975, Pat. No. 3,933,860.

[51] Int. Cl.$^3$ ............................................. C07D 307/32
[52] U.S. Cl. ............................... 260/343.6; 260/343.5; 546/205; 546/216; 549/28; 549/63

[58] Field of Search ...................................... 260/343.6

[56] References Cited

U.S. PATENT DOCUMENTS

Re. 28,242  11/1974  Boosen ............................. 260/343.6
3,576,010   4/1971   Bachman .......................... 260/343.6
4,165,322   8/1979   Reynolds, Jr. .................... 260/343.6

FOREIGN PATENT DOCUMENTS 659483  10/1951  United Kingdom ............. 260/343.6

OTHER PUBLICATIONS

Chem. Abstract: 9174e (1964).
Chem. Abstracts 69:106359p.
Chem. Abstracts 70:106242r.
Chem. Abstracts 74:22402n.
Chem. Abstracts 75:35348v.

Primary Examiner—Ethel G. Love
Attorney, Agent, or Firm—J. A. Buchanan, Jr.; T. G. DeJonghe; L. S. Squires

[57] ABSTRACT 3-(N-arylamino)-gamma-butyrolactones, butyrolactams and thiobutyrolactones are intermediates for compounds having fungicidal activity.

6 Claims, No Drawings

3-(N-ARYLAMINO)-GAMMA-BUTYROLACTONES, BUTYROLACTAMS AND THIOBUTYROLACTONES ARE INTERMEDIATES FOR COMPOUNDS HAVING FUNGICIDAL ACTIVITY

RELATED APPLICATIONS

This application is a continuation-in-part of application Ser. No. 13,856, filed Feb. 2, 1979, which in turn is a continuation-in-part of Ser. No. 847,502, filed Nov. 1, 1977, now abandoned, which in turn is a continuation-in-part of application Ser. No. 837,121, filed Sept. 29, 1977, now U.S. Pat. No. 4,141,989, which in turn is a continuation-in-part of application Ser. No. 731,491, filed Oct. 12, 1976, now U.S. Pat. No. 4,107,323, which in turn is a continuation-in-part of application Ser. No. 631,351, filed Nov. 12, 1975, now U.S. Pat. No. 4,012,519, which in turn is a continuation-in-part of application Ser. No. 548,660, filed Feb. 10, 1975, now U.S. Pat. No. 3,933,860, the disclosures of which are incorporated herein by reference.

BACKGROUND OF THE INVENTION

This invention relates to 3-(N-arylamino) lactones and thiolactones which are useful as intermediates for making fungicidal 3-(N-aryl-N-arylamino) lactones and thiolactones.

U.S. Pat. No. 3,933,860, issued Jan. 26, 1976, U.S. Pat. No. 4,012,519, issued Mar. 15, 1977, U.S. Pat. No. 4,107,323, issued Aug. 15, 1978, and U.S. Pat. No. 4,141,989, issued Feb. 27, 1979, all disclose the use of a large class of 3-(N-acyl-N-arylamino) lactones and 3-(N-acyl-N-arylamino) lactams as protectant fungicides.

U.S. Pat. No. 4,034,108, issued July 5, 1977, to H. Moser, and U.S. Pat. No. 4,015,648, issued May 24, 1977 to H. Moser, disclose the use of N-(methoxycarbonylethyl)-N-haloacetylanilines as preventive and curative fungicides.

German Patent Publication Nos. 2,643,403 and 2,643,445, published Apr. 7, 1977, disclose the use of N-(alkylthiocarbonylethyl)acetanilides for controlling fungi, particularly those of the class Phycomycetes.

Netherlands Patent Publication No. 152,849, published April 15, 1977, discloses the use of N-(alkoxymethyl)acetanilides as fungicides.

Belgin Pat. No. 867,556, published Nov. 27, 1978, discloses 3-(N-cyclopropylcarbonyl-N-arylamino)-gamma-butyrolactones.

Belgian Pat. No. 863,615, published Aug. 3, 1978, discloses fungicidal 3-(N-acyl-N-arylamino)-gamma-butyrolactones.

SUMMARY OF THE INVENTION

It has been found that 3-(N-acyl-N-arylamino)-gamma-butyrolactones, butyrolactams and butyrothiolactones are effective for the control of fungi, especially for downy mildew fungal infection caused by fungal species of the Peronosporaceae family and late blight fungal infection caused by *Phytophthora infestans*. Some of such compounds are effective both as protectant fungicides, i.e., they prevent or protect against fungal infections, and as eradicant fungicides, i.e., they eliminate and cure established infections. The compounds of the invention are useful as intermediates for making said fungicidal compounds.

DESCRIPTION OF THE INVENTION

The compounds of the invention are represented by the formula (I)

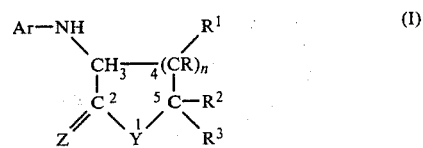

wherein Ar is phenyl, naphthyl, or phenyl or naphthyl substituted with 1 to 4 of the same or different substituents selected from fluoro, chloro, bromo, alkyl of 1 to 4 carbon atoms, alkoxy of 1 to 4 carbon atoms or nitro; R, $R^1$, $R^2$ and $R^3$ are independently hydrogen, alkyl of 1 to 6 carbon atoms, phenyl or phenyl substituted with 1 to 2 of the same or different substituents selected from fluoro, chloro, bromo or alkyl of 1 to 6 carbon atoms; Z is O or S; Y is O, S, or NR; and n is 1 or 2.

Representative substituted-phenyl groups which Ar may represent are 2-fluorophenyl, 2,4-dichlorophenyl, 3,5-dibromophenyl, 4-methylphenyl, 2,6-diethylphenyl, 4-methoxyphenyl, 4-nitrophenyl, 2,6-dimethyl-4-chlorophenyl, 2,3,6-trimethylphenyl, 2,3,5,6-tetramethylphenyl. Preferred substituted-phenyl Ar groups are phenyl substituted with 1 to 2 of the same or different substituents selected from chloro, bromo, alkyl of 1 to 4 carbon atoms or alkoxy of 1 to 4 carbon atoms. Most preferred substituted-phenyl Ar groups are 2,6-dialkylphenyl, especially 2,6-dimethylphenyl.

Representative substituted-naphthyl Ar groups are 1-naphthyl, 2-naphthyl, 1-methyl-2-naphthyl, 4-methyl-2-naphthyl, 4-methyl-1-naphthyl, 2-chloro-1-naphthyl, 2-methoxy-1-naphthyl, 2,4-dimethyl-1-naphthyl and 2,7-dimethyl-1-naphthyl. Preferred substituted naphthyl Ar groups are 2-alkyl-1-naphthyl groups, especially 2-methyl-1-naphthyl.

Representative alkyl R, $R^1$, $R^2$ and $R^3$ groups are methyl, ethyl, isopropyl and n-hexyl. Representative substituted-phenyl R, $R^1$, $R^2$ and $R^3$ groups are 2-chlorophenyl, 2,4-dichlorophenyl, 4-methyl-phenyl and 2,3-dimethylphenyl.

Preferably Ar is phenyl substituted with 1 to 2 of the same or different substituents selected from fluoro, chloro, bromo or alkyl of 1 to 2 carbon atoms, or 2-alkyl-1-naphthyl. The most preferred Ar groups are 2,6-dimethylphenyl or 2-methyl-1-naphthyl.

Preferably R, $R^1$ and $R^3$ are hydrogen.

Preferably $R^2$ is hydrogen or methyl. Preferably n=1 and Z is oxygen.

The N-phenylamino thiolactones of the invention may be represented by the formula

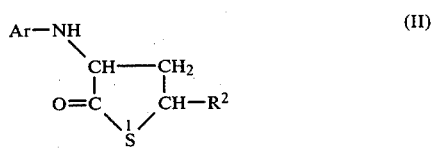

wherein Ar is phenyl or substituted phenyl as previously defined, and $R^2$ has the same significance as previously defined. In formula (II), Ar preferably is phenyl substituted with 1 to 2 of the same or different substituents selected from fluoro, chloro, bromo, alkyl of 1 to 4 carbon atoms or alkoxy of 1 to 4 carbon atoms. A preferred class of N-phenylaminothiolactones is that represented by the formula

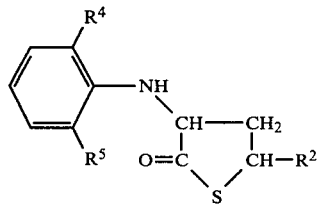

wherein $R^2$ is hydrogen or methyl, and $R^4$ and $R^5$ individually are methyl or ethyl. Particularly preferred compounds of formula (III) are those wherein $R^2$ is hydrogen and $R^4$ and $R^5$ are methyl.

The N-phenylamino lactones of the invention may be represented by the formula.

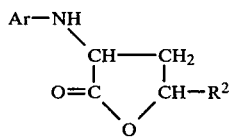

wherein Ar is phenyl or substituted phenyl as previously defined, $R^2$ has the same significance as previously defined. A preferred class of N-phenylamino-lactones is that represented by the formula

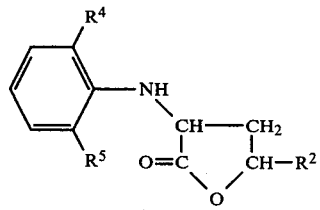

wherein $R^2$ is hydrogen or methyl, and $R^4$ and $R^5$ individually are methyl or ethyl. Preferred compounds of formula (V) are those wherein $R^2$ is hydrogen, and $R^4$ and $R^5$ are methyl.

The N-naphthylamino-lactones and thiolactones of the invention may be represented by the formula

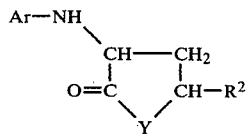

wherein Ar is naphthyl or substituted naphthyl, and wherein $R^2$ and Y have the same significance as previously defined. A preferred class of N-naphthyl amino lactones and thiolactones is that represented by the formula (VII)

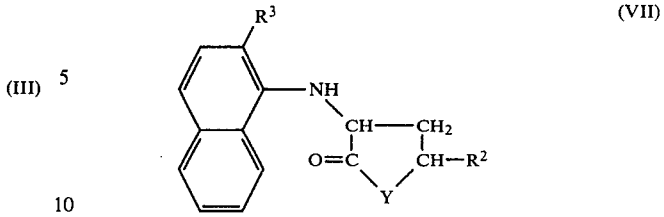

wherein $R^3$ is hydrogen or alkyl of 1 to 3 carbon atoms; and Y is oxygen or sulfur. Particularly preferred compounds of formula (VII) are those wherein $R^3$ is methyl and Y is oxygen.

Representative compounds of formula (I) include:
3-(N-phenylamino)-gamma-butyrothiolactone
3-(N-4-chlorophenylamino)-gamma-butyrothiolactone
3-(N-4-methoxyphenylamino)-gamma-butyrothiolactone
3-(N-2,6-dimethylphenylamino)-5-methyl-gamma-butyrothiolactone
3-(N-2,6-dimethylphenylamino)-gamma-butyrothiolactone
3-(N-3,4-dimethylphenylamino)-gamma-butryothiolactone
3-(N-2-methoxyphenylamino)-gamma-butyrolactone
3-(N-2-methylnaphthyl-1-amino)-5-phenyl-gamma-butryothiolactone
3-(N-2-methylnaphthyl-1-amino)-gamma-butyrothiolactone
3-(N-1-naphthylamino)-5-methyl-gamma-butyrothiolactone
3-(N-2-methylnaphthyl-1-amino)-gamma-butyrolactone and
3-(N-2,6-dimethylphenylamino)-gamma-butyrolactone.

The lactone and thiolactone compounds of the invention may be prepared by alkylating an aniline (VIII) with an alpha-halo-gamma-butyrolactone or alpha-halo-gamma-butyrothiolactone (IX). Fungicidal compounds may be obtained by subsequently acylating the alpha-(N-arylamino)-gamma-butyrolactone or butyrothiolactone (X) with an acyl halide (XI) to give the 3-(N-acyl-N-arylamino)-gamma-butyrolactone or butyrothiolactone product, as depicted by the following equations:

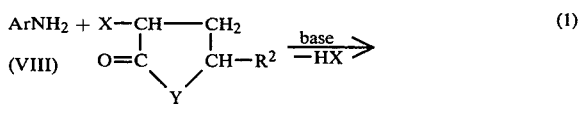

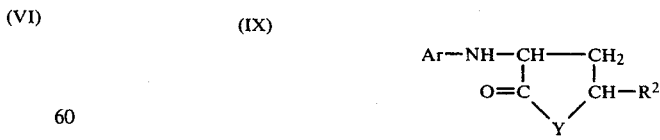

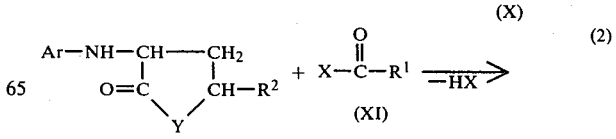

-continued

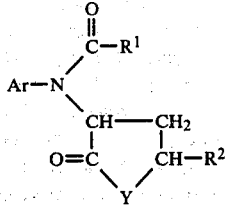

wherein Ar, $R^2$ and Y have the same significance as previously defined, and X is chloro or bromo.

The alkylation reaction (1) is conducted in the presence of a base. Suitable bases are inorganic alkali metal carbonates such as sodium carbonates or potassium carbonate or organic amines such as trialkylamines, e.g., triethylamine, or pyridine compounds, e.g., pyridine or 2,6-dimethylpyridine. Generally, substantially equimolar amounts of reactants (VIII) and (IX) and the base are employed. In one modification of the reaction, a molar excess of the aniline reactant (VIII) is used as the base, and no additional base is employed. The reaction is conducted in inert organic solvents, e.g., apolar diprotic solvents such as dimethylformamide and acetonitrile and aromatic hydrocarbons such as benzene and toluene, at reaction temperatures varying from 25° C. to 150° C., preferably from 50° C. to 150° C. Water may be employed as a co-solvent. The reaction pressure may be atmospheric, subatmospheric or superatmospheric. However, for convenience of conducting the reaction, the pressure is generally atmospheric. The reaction time will, of course, vary depending upon the reactants and the reaction temperature. Generally the reaction time is from 0.25 to 24 hours. The product (X) is generally purified by conventional procedures, e.g., extraction, distillation or crystallization, before use in the acylation reaction (2).

Preferred alkylation reaction conditions are given in more detail in the commonly assigned application of Richard N. Reynolds, Jr., entitled "Alkylation of Aniline with a Lactone in the Presence of Water", Ser. No. 847,503, filed Nov. 1, 1977.

The acylation reaction (2) is conducted by conventional procedures. The reactants (X) and (XI) are generally contacted in substantially equimolar amounts in an inert organic solvent at a temperature of 0° to 100° C. Suitable inert organic solvents include ethyl acetate, methylene dichloride, dimethoxyethane, benzene, etc. The product is isolated and purified by conventional procedures such as extraction, distillation, chromatography, crystallization, etc.

When preparing a butyrolactone product (compounds of Formula (I) wherein Y=O), an organic amine such as trialkylamine or a pyridine compound may be employed as an acid acceptor. However, when preparing a butyrothiolactone product (compounds of Formula (I) wherein Y=S), an organic amine should not be employed.

Preferred acylation reaction conditions are given in more detail in the commonly assigned application of Richard N. Reynolds, Jr., Stephen D. Ziman and David C. K. Chan, entitled "Acylation of Lactone-Substituted Aniline Compound in the Absence of an Acid-Acceptor", Ser. No. 847,504, filed Nov. 1, 1977, now abandoned.

The compounds of the invention are useful as intermediates for making fungicidal compounds. For example, the fungicidal compounds disclosed is U.S. Pat. Nos. 4,141,989, 4,107,323, 4,012,519 and 3,933,860 may be made employing the compounds of the invention. The compounds of Belgian Pat. Nos. 867,556 and 863,615 may also be made employing the compounds herein as intermediates.

EXAMPLES

The preparation of the compounds of the invention is illustrated by the following examples.

EXAMPLE 1

Preparation of 3-(N-chloroacetyl-N-2,6-dimethylphenyl)-gamma-butyrothiolactone

A solution of 10 g (0.055 mol) alpha-bromo-gamma-butyrothiolactone, 6.68 g (0.055 mol) 2,6-dimethylaniline and 5.58 g (0.055 mol) dimethylpyridine was heated at 85°–90° C. for 12 hours. The reaction mixture was then cooled, diluted with water and dichloromethane. The organic phase was separated and filtered through a short silica gel column. The filtrate was evaporated under reduced pressure to give an oil residue. The residue was washed with 5% aqueous hydrochloric acid solution, washed with water, and dried over magnesium sulfate to give 7.2 g of 3-(N-2,6-dimethylphenylamino)-gamma-butyrothiolactone. The infrared spectrum of the thiolactone product showed strong carbonyl absorption at 5.88 micron. Elemental analysis for $C_{12}H_{15}NOS$ showed: %S, calc. 14.5, found 14.2.

A solution of 1.52 g (0.0134 mol) chloroacetylchloride in 10 ml toluene was added dropwise to a solution of 2.97 g (0.0134 mol) 3-(N-2,6-dimethylphenylamino)-gamma-butyrothiolactone in 100 ml benzene maintained at reflux temperature. The reaction mixture was heated at reflux until the evolution of hydrochloride gas ceased (about 3 hours), cooled, and evaporated under reduced pressure to give a brown solid. Recrystallization from isopropanol gave 2.5 g of 3-(N-chloroacetyl-N-2,6-dimethylphenylamino)-gamma-butyrothiolactone, as tan crystals, m.p. 138°–139° C. The infrared spectrum of the product showed two strong carbonyl absorption bands at 5.88 microns and 6.02 microns. The product is tabulated in Table A as Compound No. A-1.

EXAMPLE 2

Preparation of 3-(N-chloro-acetyl-N-2-chloro-6-methylphenylamino)-gamma-butyrothiolactone A solution of 8 g (0.044 mol) alpha-bromo-gamma-butyrothiolactone, 6.23 g (0.044 mol) 2-chloro-6-methylaniline and 4.7 g (0.044 mol) 2,6-dimethylpyridine was heated for about 16 hours at about 95° C. under a nitrogen atmosphere. The reaction mixture was cooled, diluted with 60 ml dichloromethane, washed with water, washed with 10% aqueous hydrochloric acid, and filtered. The filtrate was dried over magnesium sulfate and evaporated under reduced pressure to give a dark viscous residue. The residue was eluted through a short silica gel chromatography column with dichloromethane. The product-containing fractions were stripped to give 4.59 g of 3-(N-2-chloro-6-methylphenylamino)-gamma-butyrothiolactone. Thin-layer chromatography of the product showed one large spot. The infrared spectrum of the product showed strong carbonyl absorption at 5.88 microns and the nuclear magnetic resonance spectrum showed a 3-proton singlet for the methyl group at 2.33 ppm (relative to tetramethylsilane).

A solution of 2.15 g (0.019 mol) chloroacetyl chloride in 10 ml toluene was added dropwise to a refluxing solution of 4.59 g (0.019 mol) 3-(N-2-chloro-6-methylphenylamino)-gamma-butyrothiolactone in 150 ml toluene. The reaction mixture was heated at reflux for about 7 hours (HCl was evolved), stirred about 16 hours at 25° C. and evaporated under reduced pressure to give a dark residue. Thin-layer chromatography of the residue showed two spots. The residue was chromatographed through a silica-gel column with acetone/dichloromethane elution. The chromatographic fractions containing the second material eluted from the column were combined and evaporated to give the desired product, which was crystallized from isopropyl alcohol to give 0.98 g of product, as a brown solid, m.p. 133°–137° C. The infrared spectrum of the product showed two strong carbonyl absorption bands at 5.84 microns and 5.95 microns. The compound is tabulated in Table A as Compound No. A-3.

EXAMPLE 3

Preparation of 3-(N-methoxyacetyl-N-2,6-dimethylphenylamino)-gamma-butyrothiolactone A solution of 1.46 g (0.0135 mol) methoxyacetyl chloride in 10 ml dichloromethane was added dropwise to a refluxing solution of 3 g (0.0135 mol) 3-(N-2,6-dimethylphenylamino)-gamma-butyrothiolactone in 200 ml toluene. The reaction mixture was heated at reflux for 3 hours and evaporated to give a solid. The solid was recrystallized from a 10:1:10 solvent mixture of ether:benzene:hexane to give 1.8 g of the product, as a tan solid, m.p. 86°–87° C. The infrared spectrum of the product showed two strong carbonyl absorption bands at 5.85 microns and 6.03 microns. The product is tabulated in Table A as Compound No. A-4.

EXAMPLE 4

Preparation of 3-(N-chloroacetyl-N-2,6-dimethylphenylamino)-5-chloro-gamma-butyrolactone A slurry of 16 g (0.06 mol) of 3-(N-chloroacetyl-N-2,6-dimethylphenylamino)-gamma-butyrolactone, 11 g (0.08 mol) N-chlorosuccinimide and 0.5 g benzoyl peroxide in 200 ml carbon tetrachloride was heated under reflux for 18 hours. The reaction mixture was cooled to about 25° C. A solid separated. The solid was filtered from the reaction mixture and washed with 200 ml dichloromethane. The mother liquor was washed with water, dried over magnesium sulfate and evaporated under reduced pressure to give an oil residue. The residue was crystallized from ether to give 19.5 g of product, m.p. 103°–106° C. This product is tabulated in Table B as Compound No. B-1.

EXAMPLE 5

Preparation of 3-(N-acetoxyacetyl-N-2,6-dimethylphenylamino)-gamma-butyrolactone A 13.7 g (0.1 mol) sample of acetoxyacetyl chloride was added dropwise to a solution of 20.5 g (0.1 mol) N-2,6-dimethylphenylamino-gamma-butyrolactone and 7.9 g (0.1 mol) pyridine in 150 ml benzene. After completion of the addition, the reaction mixture was stirred at about 25° C. for 4 hours, then washed with water, dried over magnesium sulfate and evaporated under reduced pressure to give an oily residue. The residue was crystallized from ethyl ether/hexane to give 27.3 g of product, m.p. 90°–91° C. This product is tabulated in Table B as Compound No. B-2.

3-(N-cyclopropylcarbonyl-N-2,6-dimethylphenylamino)-gamma-butyrolactone can be made in an analogous manner using cyclopropylcarbonyl chloride and N-2,6-dimethylphenylamino-gamma-butyrolactone as starting materials.

EXAMPLE 6

Preparation of N-hydroxyacetyl-N-2,6-dimethylphenylamino-gamma-butyrolactone A solution of 50 g (0.18 mol) 3-(N-chloroacetyl-N-2,6-dimethylphenylamino)-gamma-butyrolactone, 14.5 g (0.36 mol) sodium hydroxide dissolved in 50 ml water, and 450 ml dimethoxyethane was stirred at about 25° C. for 16 hours. The resulting reaction mixture was filtered, diluted with 500 ml dichloromethane. Hydrogen chloride gas was bubbled into the reaction mixture for 1 hour. The reaction mixture was filtered, dried over magnesium sulfate, and evaporated under reduced pressure. The residue was washed with 10% ethyl ether/90% hexane, filtered and air-dried to give 36.5 g of the product as a white crystalline solid, m.p. 173°–174° C. The product is tabulated in Table B as Compound No. B-3.

EXAMPLE 7

Preparation of N-ethoxyacetyl-N-2,6-dimethylphenylamino-gamma-butryolactone

A 6.2 g (0.05 mol) sample of ethoxyacetyl chloride was added dropwise to a refluxing solution of 10.3 (0.05 mol) 3-(N-2,6-dimethylphenylamino)-gamma-butyrolactone in 150 ml toluene. The reaction mixture was then heated under reflux for 2 hours. After cooling, the reaction mixture was washed with water, washed with saturated sodium bicarbonate solution, washed with water, dried over magnesium sulfate and evaporated to give 11.2 g of 3-(N-ethoxyacetyl-N-2,6-dimethylphenylamino)-gamma-butyrolactone, m.p. 73°–75° C. The product is tabulated in Table B as Compound No. B-9.

EXAMPLE 8

Preparation of N-methylthioacetyl-N-2,6-dimethylphenylamino-gamma-butyrolactone A 22 g (0.3 mol) sample of sodium methylmercaptide was added in small portions to a solution of 25.3 g (0.08 mol) N-bromoacetyl-N-2,6-dimethylphenylamino)-gamma-butyrolactone, m.p. 116°–117° C., in 200 ml dimethyl sulfoxide. A mild exotherm ensued. The reaction mixture was allowed to stir at about 25° C. for about 16 hours. The reaction mixture was then heated to about 150° C. under reduced water aspirator pressure to remove a portion of the dimethyl sulfoxide solvent. The residue was diluted with water and the aqueous layer separated. The organic portion was dissolved in 350 ml dichloromethane, washed with water, dried over magnesium sulfate and evaporated under reduced pressure to give an oil. The oil was chromatographed through a silica gel column (20% acetone/80% petroleum ether elution) to give the product (11 g), which after crystallization from ethyl ether/acetone melted at 77°–78° C. The product is tabulated in Table as Compound No. B-6.

EXAMPLE 9

Preparation of 3-(N-chloroacetyl-N-2-methylnaphthyl-1-amino)-gamma-butyrolactone A 200 ml round-bottom flask equipped with heating mantle and connected to a water aspirator vacuum system was charged with 15.0 g (0.1 mcl) 1-amino-2-methylnaphthalene, 16.4 g (0.1 mol) alpha-bromo-gamma-butyrolactone and 10.7 g (0.1 mol) 2,6-dimethylpyridine. The reaction mixture was maintained at about 94°–101° C. and 160 mm of Hg for about 7 hours. The reaction mixture was cooled, diluted with 100 ml acetone and filtered. The filtrate was evaporated under reduced pressure to give an oily residue which was eluted through a silica gel column with 15% acetone/85% petroleum ether to give 14.6 g of 3-(N-2-methylnaphthyl-1-amino)-gamma-butyrolactone, m.p. 92°–94° C. Elemental analysis for $C_{15}H_{15}NO_2$ showed: %C, calc. 75.0, found 74.5; %H, calc. 5.9, found 5.6; %N, calc. 5.8, found 5.6.

A 2.4 g (0.021 mol) sample of chloroacetyl chloride was added to a refluxing solution of 5.0 g (0.021 mol) 3-(N-2-methylnaphthyl-1-amino)-gamma-butyrolactone in 100 ml toluene. The reaction mixture was heated under reflux for 30 minutes. Gas was evolved and a white precipitate formed during the 30-minute reflux period. The reaction mixture was cooled, washed with water, dried over magnesium sulfate and evaporated under reduced pressure to give 4.3 g of product, as a white solid, m.p. 121°–122° C. The infrared spectrum of the product showed two strong carbonyl absorption bands at 5.62 microns and 5.88 microns. The product is tabulated in Table C as Compound No. C-1.

EXAMPLE 10

Preparation of 3-(N-methoxy-acetyl methyl-N-2-methylnaphthyl-1-amino)-gamma-butyrolactone A 2.4 g (0.022 mol) sample of methoxyacetyl chloride was added dropwise to a solution of 5.5 g (0.022 mol) 3-(N-2-methylnaphthyl-1-amino)-gamma-butyrolactone and 1.7 g (0.022 mol) pyridine in 100 ml dichloromethane. The reaction mixture was stirred one hour at about 25° C. and then heated under reflux for 6 hours. After cooling overnight, the reaction mixture was washed successively with water, saturated sodium bicarbonate solution, water, dried over magnesium sulfate and evaporated under reduced pressure. The residue was chromatographed through a silica gel column. Elution with 25% acetone/75% petroleum either gave 4.3 g of the product, m.p. 42°–46° C. The product is tabulated in Table C as Compound No. C-2.

The compounds tabulated in Tables A, B and C were prepared by procedures similar to those of Examples 1–10. The structure of each compound tabulated in Tables A, B and C was confirmed by nuclear magnetic resonance spectroscopy and/or infrared spectral analysis.

EXAMPLE 11

Preventative Tomato Late Blight

Compounds of the examples were tested for the preventative control of the Tomato Late Blight organism *Phytophthora infestans*. Five- to six-week-old tomato (cultivar Bonny Best) seedlings were used. The tomato plants were sprayed with a 250 ppm suspension of the test compound in acetone, water and a small amount of a nonionic emulsifier. The sprayed plants were then inoculated one day later with the organism, placed in an environmental chamber and incubated at 66°–68° F. and 100% relative humidity for at least 16 hours. Following the incubation, the plants were maintained in a greenhouse at 60–80% relative humidity for approximately 7 days. The percent disease control provided by a given test compound was based on the percent disease reduction relative to untreated check plants. The results are tabulated in Table I. In Table I, the test concentration is 250 ppm unless otherwise indicated by the figures in parentheses.

EXAMPLE 12

Eradicant Tomato Late Blight Control

Several compounds of the examples were tested for the eradicant control of the Tomato Late Blight organism *Phytophthora infestans*. Five- to six-week-old tomato (cultivar Bonny Best) plants were used. The tomato plants were inoculated with the organism, placed in an environmental chamber and incubated at 18°–22° C. and 100% relative humidity for 2 days. The plants were then sprayed with a 250 ppm suspension of the test compound in acetone, water and a small amount of a nonionic emulsifier. The sprayed plants were allowed to dry and then were maintained in a greenhouse at 18°–22° C. and at 95–100% relative humidity. Seven days after inoculation, the plants were observed for fungal infections. The amount of disease control provided by a given test compound was based on the amount of disease reduction relative to untreated check plants. The results are tabulated in Table I. In Table I, the test concentration is 250 ppm unless otherwise indicated by the figures in parentheses.

EXAMPLE 13

Preventative Grape Downy Mildew Control

The compounds of the example were tested for the control of the grape downy mildew organism *Plasmopara viticola*. Detached leaves, between 70 and 85 mm in diameter, of 7-week-old *Vitis vinifera* cultivar Emperor grape seedlings were used as hosts. The leaves were sprayed with a solution of the test compound in acetone. The sprayed leaves were dried, inoculated with a spore suspension of the organism, placed in a humid environmental chamber and incubated at 18°–22° C. and about 100% relative humidity. Seven to nine days after inoculation, the amount of disease control was determined. The percent disease control provided by a given test compound was based on the percent disease reduction relative to untreated check plants. The results are tabulated in Table I.

EXAMPLE 14

Eradicant Grape Downy Mildew Control

The compounds of the examples were tested for the eradicant control of the grape downy mildew organism

*Plasmopara viticola*. Detached leaves of between 70 and 85 mm diameter of 7-week-old *Vitis vinifera* cultivar Emperor grape seedlings were used as hosts. The leaves were inoculated with the organism and placed in an environmental chamber and incubated at 18°–22° C. and at about 100% relative humidity for 2 days. The leaves were then sprayed with a solution of the test compound in acetone. The sprayed leaves were then maintained at 18°–22° C. and at about 100% relative humidity. Seven to nine days after inoculaton, the amount of disease control was determined. The percent disease control provided by a given test compound was based on the percent disease reduction relative to nontreated check plants. The results are tabulated in Table I.

EXAMPLE 15

Systemic Soil Drench Treatment for Safflower Crown and Root Rot Control

Compound B-4 (4-methoxyacetyl-N-2,6-dimethylphenylamino-gamma-butyrolactone) was tested to determine its systemic activity in soil-drench applications against the safflower crown and root rot organisms, *Phytophthora cryptogea* and *P. parasitica*.

Two-week-old safflower seedlings were used as hosts. Pots containing the seedlings were drenched with an aqueous suspension of the test compound at various test concentrations (four pots per concentration level). One day after treatment a spawn of the organism was poured on the soil surface in the pots. The spawn was prepared by cultivating the organism in a mixture of oat flakes, potato dextrose and soil. The inoculated seedlings were then maintained in a greenhouse at 20°–25° C. day and 15°–20° C. night temperature. Three to four weeks after inoculation, the plant roots and crown were rated for disease. The percent disease control provided by the test compound was based on percent disease reduction relative to nontreated check plants. The test concentrations and the percent disease control are tabulated in Table II.

TABLE A

Compounds of the Formula $$\begin{array}{c} \text{Ar—N} \begin{array}{c} \text{C—R}^1 \\ \parallel \\ \text{O} \end{array} \\ \text{CH——CH}_2 \\ \text{O=C} \quad \text{CH}_2 \\ \diagdown \text{S} \diagup \end{array}$$

| No. | Ar | R$^1$ | Melting Point, C. | Cl Calc. | Cl Found | S Calc. | S Found |
|---|---|---|---|---|---|---|---|
| A-1 | 2,6-(CH$_3$)$_2\phi$ | ClCH$_2$ | 130–131 | 11.9 | 13.1 | 10.8 | 11.7 |
| A-2 | 2,6-(CH$_3$)$_2\phi$ | CH$_3$CO$_2$CH$_2$ | 124–125 | — | — | 10.0 | 10.2 |
| A-3 | 2-Cl—6-CH$_3\phi$ | ClCH$_2$ | 133–137 | 22.3 | 23.6 | 10.0 | 11.0 |
| A-4 | 2,6(CH$_3$)$\phi$ | CH$_3$OCH$_2$ | 86–87 | — | — | 10.9 | 11.2 |
| A-5 | 2-Cl—6-CH$_3\phi$ | CH$_3$CO$_2$CH$_2$ | 99–100 | 10.4 | 11.7 | 9.4 | 9.1 |
| A-6 | 3,4-(Cl)$_2\phi$ | ClCH$_2$ | oil | 31.5 | 32.7 | 9.4 | 9.3 |
| A-7 | 2,6-(C$_2$H$_5$)$_2\phi$ | ClCH$_2$ | 108–114 | 10.9 | 12.6 | 9.8 | 10.3 |
| A-8 | 2,6-(C$_2$H$_5$)$_2\phi$ | CH$_3$CCH$_2$ | 74–82 | — | — | 10.0 | 10.6 |
| A-9 | 2,3-(CH$_3$)$_2\phi$ | ClCH$_2$ | 99–102 | 11.9 | 11.7 | 10.8 | 10.2 |
| A-10 | 2,3-(CH$_3$)$_2\phi$ | CH$_3$OCH$_2$ | oil | — | — | 10.9 | 10.3 |
| A-11 | 2-CH$_3$—6-C$_2$H$_5\phi$ | ClCH$_2$ | 110–120 | 57.8 | 57.8$^1$ | 5.8 | 5.8$^2$ |
| A-12 | 2-CH$_3$—6-C$_2$H$_5\phi$ | CH$_3$OCH$_2$ | 88–90 | 62.4 | 62.5$^1$ | 6.8 | 6.8$^2$ |
| A-13 | 2,3,6-(CH$_3$)$_3\phi$ | CH$_3$OCH$_2$ | 101–103 | 62.5 | 60.2$^1$ | 6.8 | 6.7$^2$ |
| A-14 | 2,3,6-(CH$_3$)$_3\phi$ | ClCH$_2$ | 104–107 | 57.8 | 56.5$^1$ | 5.8 | 5.8$^2$ |
| A-15 | 2,3,5,6-(CH$_3$)$_4\phi$ | ClCH$_2$ | 140–143 | 59.0 | 60.1$^1$ | 6.1 | 6.3$^2$ |
| A-16 | 2,3,5,6-(CH$_3$)$_4\phi$ | CH$_3$OCH$_2$ | 122–123 | 63.6 | 65.8$^1$ | 7.2 | 7.4$^2$ |

[1] Carbon
[2] Hydrogen
$\phi$ = Phenyl

TABLE B

Compounds of the Formula $$\begin{array}{c} \text{Ar—N} \begin{array}{c} \text{C—R}^1 \\ \parallel \\ \text{O} \end{array} \\ \text{CH——CH}_2 \\ \text{O=C} \quad \text{CH—R}^2 \\ \diagdown \text{O} \diagup \end{array}$$

| No. | Ar | R$^1$ | R$^2$ | m.p., °C. | C Cal. | C Fd. | H Cal. | H Fd. | N Cal. | N Fd. | X Cal. | X Fd. |
|---|---|---|---|---|---|---|---|---|---|---|---|---|
| B-1 | (1) | ClCH$_2$ | Cl | 103–106 | — | — | — | — | — | — | 22.4 | 21.0$^1$ |
| B-2 | (1) | CH$_3$CO$_2$CH$_2$ | H | 90–91 | 63.0 | 63.3 | 6.3 | 6.7 | 4.6 | 4.5 | — | — |
| B-3 | (1) | HOCH$_2$ | H | 173–174 | 63.9 | 63.2 | 6.5 | 6.6 | 5.3 | 4.4 | — | — |
| B-4 | (1) | CH$_3$OCH$_2$ | H | 133–134 | 65.0 | 65.5 | 6.9 | 6.8 | 5.1 | 5.2 | — | — |
| B-5 | (1) | $\phi$SCH$_2$ | H | 84–86 | — | — | — | — | — | — | 8.9 | 9.0$^2$ |

TABLE B-continued

Compounds of the Formula $$\text{Ar}-\text{N}\begin{pmatrix} \text{C(=O)}-\text{R}^1 \\ \text{CH}-\text{CH}_2 \\ | \quad \quad | \\ \text{O=C} \quad \text{CH}-\text{R}^2 \\ \backslash \text{O} / \end{pmatrix}$$

| No. | Ar | R$^1$ | R$^2$ | m.p., °C. | C Cal. | C Fd. | H Cal. | H Fd. | N Cal. | N Fd. | X Cal. | X Fd. |
|---|---|---|---|---|---|---|---|---|---|---|---|---|
| B-6 | (1) | CH$_3$SCH$_2$ | H | 77–78 | — | — | — | — | — | — | 10.9 | 9.1$^2$ |
| B-7 | (2) | ClCH$_2$ | H | oil | — | — | — | — | — | — | 9.2 | 11.1$^1$ |
| B-8 | (2) | CH$_3$OCH$_2$ | H | oil | 67.0 | 66.0 | 7.2 | 7.2 | 4.8 | 4.0 | — | — |
| B-9 | (1) | CH$_3$CH$_2$OCH$_2$ | H | 73–75 | 66.0 | 66.0 | 7.3 | 7.2 | 4.8 | 5.0 | — | — |
| B-10 | (3) | ClCH$_2$ | H | 128–130 | — | — | — | — | — | — | 11.5 | 13.2$^1$ |
| B-11 | (3) | CH$_3$OCH$_2$ | H | 104–105 | 66.9 | 67.5 | 7.5 | 7.5 | 4.6 | 4.5 | — | — |
| B-12 | (1) | i-C$_3$H$_7$OCH$_2$ | H | oil | 66.9 | 66.9 | 7.6 | 7.5 | 4.6 | 4.1 | — | — |
| B-13 | (1) | ClCH$_2$ | Br | 98–102 | 46.6 | 47.7 | 4.2 | 4.4 | 3.9 | 4.2 | — | — |

(1) 2,6-(CH$_3$)$_2\phi$
(2) 2,3,6-(CH$_3$)$_3\phi$
(3) 2,3,4,5-(CH$_3$)$_4\phi$
$^1$Chlorine
$^2$Sulfur

TABLE C

Compounds of the Formula $$\text{Ar}-\text{N}\begin{pmatrix} \text{C(=O)}-\text{R}^1 \\ \text{CH}-\text{CH}_2 \\ | \quad \quad | \\ \text{O=C} \quad \text{CH}_2 \\ \backslash \text{O} / \end{pmatrix}$$

| No. | Ar | R$^1$ | Melting Point, °C. | C Cal. | C Fd. | H Cal. | H Fd. | N Cal. | N Fd. | X Cal. | X Fd. |
|---|---|---|---|---|---|---|---|---|---|---|---|
| C-1 | (1) | ClCH$_2$ | 121–122 | — | — | — | — | — | — | 11.2 | 12.5(Cl) |
| C-2 | (1) | CH$_3$OCH$_2$ | 42–46 | 69.0 | 72.6 | 6.1 | 6.6 | 4.5 | 4.5 | — | — |
| C-3 | (1) | BrCH$_2$ | 116–118 | — | — | — | — | — | — | 22.1 | 21.5(Br) |
| C-4 | (1) | CH$_3$SCH$_2$ | 52–55 | 65.6 | 62.3 | 5.8 | 5.4 | — | — | — | — |
| C-5 | (2) | ClCH$_2$ | 110–113 | 63.3 | 63.3 | 4.7 | 4.8 | 4.6 | 4.5 | — | — |
| C-6 | (2) | CH$_3$OCH$_2$ | 109–111 | 68.2 | 69.6 | 5.7 | 5.9 | 4.7 | 5.3 | — | — |

(1) 1-(2-methylnaphthyl)
(2) 1-(naphthyl)

TABLE I

| No. | Tomato Late Blight Preventative (ppm) | Tomato Late Blight Eradicative (ppm) | Grape Downy Mildew Preventative (ppm) | Grape Downy Mildew Eradicative (ppm) |
|---|---|---|---|---|
| A-1 | 98 | 84(100) | 82(40) | 5(100) |
| A-2 | 14 | — | — | 3(100) |
| A-3 | 100 | 42(100) | — | 7(100) |
| A-4 | 96(40) | 81(100) | 98(100) | 10(100) |
| A-5 | 29 | — | — | 0(100) |
| A-6 | 23 | — | — | 0(100) |
| A-7 | 98 | 54 | 93(16) | 80(16) |
| A-8 | 26(100) | — | — | 0(100) |
| A-9 | 68(40) | — | — | 12(100) |
| A-10 | 89(100) | 95 | — | 80(100) |
| A-11 | 80 | — | — | — |
| A-12 | 89 | — | — | — |
| A-13 | 100 | — | — | — |
| A-14 | 100 | — | — | — |
| A-15 | 37 | — | — | — |
| A-16 | 100 | — | — | — |
| B-1 | 100 | 92(100) | 0(100) | 88(100) |
| B-2 | 88 | — | — | 9(100) |
| B-3 | 92(100) | 92(100) | — | 0(100) |
| B-4 | 88(16) | 96(40) | 100(40) | 95(16) |
| B-5 | 84 | 58 | — | 73(100) |
| B-6 | 97 | 96 | — | 54(100) |
| B-7 | 77 | — | — | — |
| B-8 | 100 | 93(100) | — | — |
| B-9 | 97 | — | — | — |
| B-10 | 37 | — | — | — |
| B-11 | 100 | — | — | — |
| B-12 | 95 | — | — | — |
| C-1 | 100 | 55(100) | 96(16) | 84(16) |
| C-2 | 0 | — | — | — |

TABLE II

Safflower Crown and Root Rot Control by Soil Drench

| Compound | Conc. ppm | % Control P. Cryptogea | P. Parasitica |
|---|---|---|---|
| Compound B-4 | 100* | 98 | 100 |
|  | 40 | 78 | 100 |
|  | 16 | 14 | 97 |
| Standard** (5-ethoxy-3- | 100 | 78 | 98 |
| trichloromethyl-1,2,4- | 40 | 12 | 78 |
| thiadiazole) | 16 | 0 | 17 |

*100 ppm = 50 micrograms/cm$^2$ = 4.46 lbs/acre

**U.S. Pat. Nos. 3,260,588 and 3,260,725

What is claimed is:

1. A compound represented by the formula

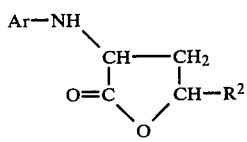
(IV)

wherein Ar is is naphthyl, or phenyl or naphthyl substituted with 1 to 4 of the same or different substituents selected from fluoro, chloro, bromo, alkyl of 1 to 4 carbon atoms, alkoxy of 1 to 4 carbon atoms or nitro; and $R^2$ is hydrogen or methyl.

2. The compound of claim 1 represented by the formula

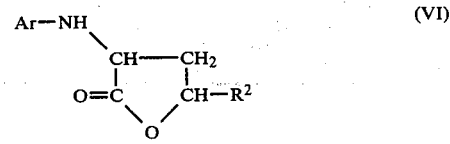
(V)

wherein $R^2$ is hydrogen or methyl, and $R^4$ and $R^5$ individually are methyl or ethyl.

3. The compound of claim 2 wherein $R^2$ is hydrogen, and $R^4$ and $R^5$ are methyl.

4. The compound of claim 1 represented by the formula (VI)

wherein Ar is naphthyl or substituted naphthyl as defined in claim 1 and $R^2$ has the same significance as defined in claim 1.

5. The compound of claim 4 represented by the formula

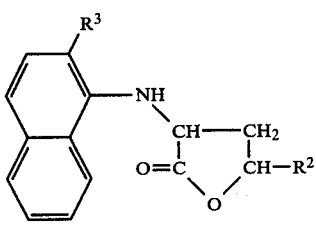
(VII)

wherein $R^3$ is hydrogen or alkyl of 1 to 3 carbon atoms.

6. The compound of claim 5 wherein $R^2$ is hydrogen and $R^3$ is methyl.

* * * * *